United States Patent
Wallwiener et al.

(10) Patent No.: US 8,894,677 B2
(45) Date of Patent: Nov. 25, 2014

(54) SPACER FOR A MEDICAL INSTRUMENT

(75) Inventors: Diethelm Wallwiener, Leimen (DE); Sara Brucker, Gomaringen/Stockach (DE)

(73) Assignee: Karl Storz GmbH & Co. KG (DE)

( * ) Notice: Subject to any disclaimer, the term of this patent is extended or adjusted under 35 U.S.C. 154(b) by 1444 days.

(21) Appl. No.: 11/517,241

(22) Filed: Sep. 7, 2006

(65) Prior Publication Data

US 2007/0210018 A1 Sep. 13, 2007

(30) Foreign Application Priority Data

Sep. 9, 2005 (DE) .......................... 10 2005 044 364

(51) Int. Cl.
*A61B 17/32* (2006.01)
*A61B 17/29* (2006.01)
*A61B 19/00* (2006.01)
*A61B 17/34* (2006.01)

(52) U.S. Cl.
CPC ............. *A61B 17/3417* (2013.01); *A61B 17/29* (2013.01); *A61B 2019/304* (2013.01); *A61B 2019/462* (2013.01); *A61B 17/320016* (2013.01); *A61B 2019/306* (2013.01); *A61B 2017/3492* (2013.01)
USPC ..................................................... 606/172

(58) Field of Classification Search
USPC ............................ 606/172; 548/188.2–188.4; 248/188.2–188.4
See application file for complete search history.

(56) References Cited

U.S. PATENT DOCUMENTS

| | | | |
|---|---|---|---|
| 4,516,968 A * | 5/1985 | Marshall et al. ............... | 604/174 |
| 4,759,363 A | 7/1988 | Jensen | |
| 5,023,406 A * | 6/1991 | Thornley ....................... | 174/209 |
| 5,057,085 A | 10/1991 | Kopans ......................... | 604/173 |
| 5,105,807 A | 4/1992 | Kahn et al. ................ | 128/207.18 |
| 5,354,283 A | 10/1994 | Bark et al. ..................... | 604/180 |
| 5,382,250 A * | 1/1995 | Kraus ............................. | 606/80 |
| 6,716,215 B1 | 4/2004 | David et al. | |
| 7,276,075 B1 * | 10/2007 | Callas et al. .................. | 606/191 |
| 2002/0111563 A1 | 8/2002 | Hall | |

FOREIGN PATENT DOCUMENTS

| | | |
|---|---|---|
| DE | 30 48 758 | 7/1982 |
| DE | 86 25 288 | 7/1987 |
| DE | 693 03 172 | 1/1997 |
| DE | 202 09 525 | 11/2002 |
| EP | 0 655 003 | 3/1994 |
| EP | 1 029 509 | 8/2000 |
| WO | WO 01/06966 | 2/2001 |

OTHER PUBLICATIONS

Storz; Karl Storz-Endoskope; The Diamond Standard; Catalog Endoworld Gyn 20-1-E/11-2004, 11 pages.
European Search Report, Jan. 9, 2007, 7 pages.

* cited by examiner

*Primary Examiner* — Thomas McEvoy
*Assistant Examiner* — Julie A Szpira
(74) *Attorney, Agent, or Firm* — St. Onge Steward Johnston & Reens LLC

(57) ABSTRACT

The spacer serves for limiting the depth of insertion of a shaft of a medical instrument into a body of a patient. The spacer has a distal abutment for bearing on a body of a patient. The spacer has a spacer element extending along a length section of the shaft of the medical instrument. A device for releasably mounting the spacer on the shaft has an aperture via which the spacer can be mounted laterally to the shaft. For it the aperture is designed as a lateral slit aperture.

18 Claims, 5 Drawing Sheets

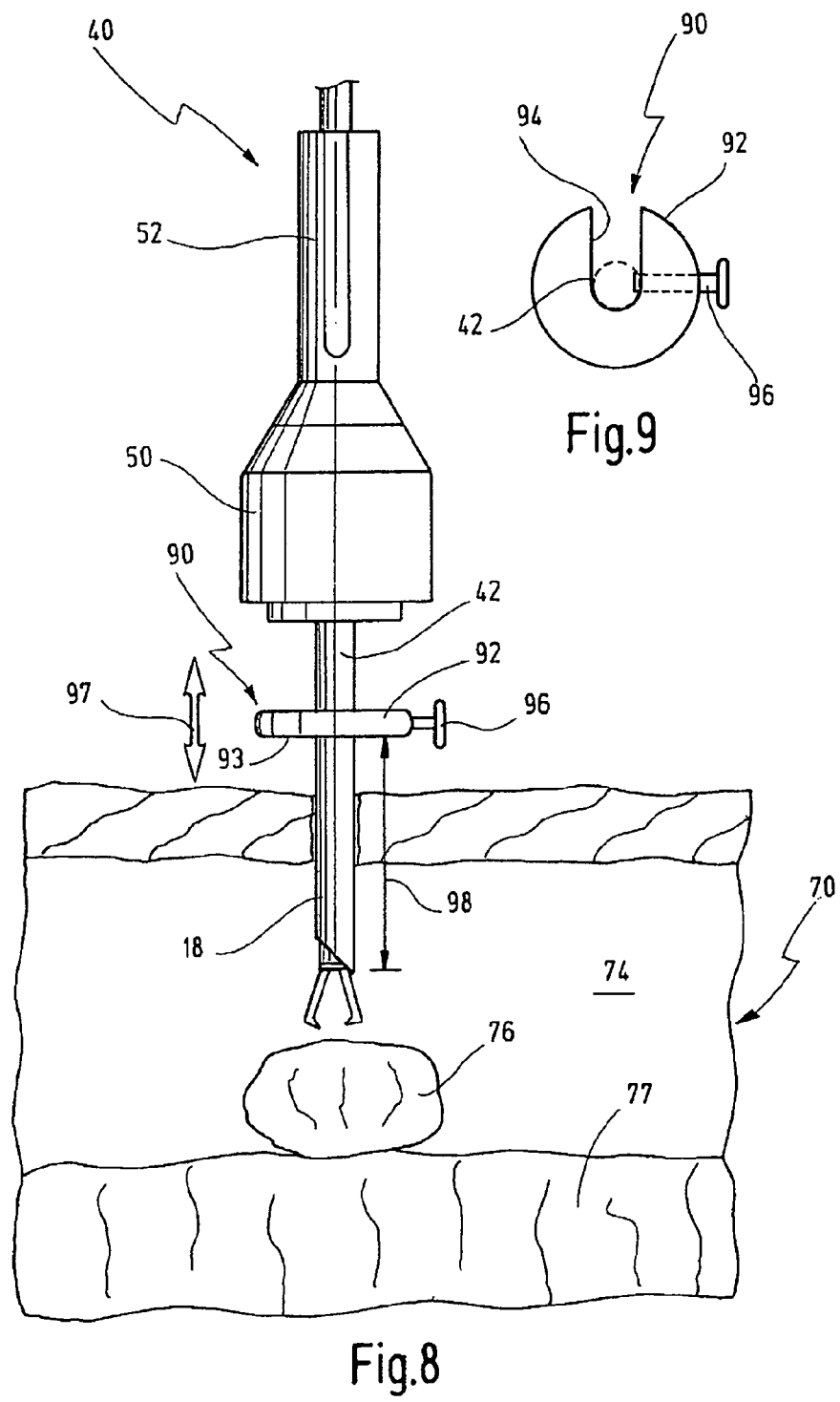

SPACER FOR A MEDICAL INSTRUMENT

BACKGROUND OF THE INVENTION

The invention relates to a spacer for limiting the depth of insertion of a shaft of a medical instrument into a body.

In minimally invasive surgery, medical instruments have become established that can be introduced into the body through a small incision, for the purpose of carrying out an intervention in the interior of the body.

The medical instruments have a shaft which is guided through the incision and into the body, for example through the abdominal wall and into the abdominal cavity. Natural orifices such as the vagina or anus can also be used for introducing Instruments of this kind. The shaft itself can be of a solid design, for example in the case of a liver retractor, a trocar mandrel or other maneuvering instruments, or it can be designed as a hollow shaft.

Different types of instruments for surgeries can be guided through the hollow shaft.

At the proximal end, the shaft in most cases terminates in a structural part of greater diameter, for example a housing, a handle or the like.

The shaft has a defined length and can in theory be pushed into the body until the instrument's structural part of greater diameter at the proximal end comes to lie on the body in the area around the opening, whether an incision or a natural orifice.

If, during a surgery, instruments are pushed through a hollow shaft that are intended to perform a tissue-removing function at a site within the body, the distance of this site from the outer surface of the body, which outer surface limits the maximum depth of insertion, varies from patient to patient.

It is of course possible to set certain maximum depths of insertion through the choice of length of the shaft, but the insertion depth is nevertheless a variable parameter depending on the operation, on the anatomical circumstances and in particular also on the size and stature of the patient.

The surgeon therefore has to take particular care to ensure that the shaft does not go beyond a defined depth of insertion.

One example is the depth of insertion of the trocar sleeve when fitting a trocar. Trocars usually comprise a hollow shaft which is closed off at the proximal end by a valve housing of greater diameter. To fit the trocar in the body, a pointed trocar mandrel is inserted into the trocar sleeve, the sharp point of the trocar mandrel protruding from the distal end of the trocar sleeve, that is to say of the shaft. This trocar mandrel point is placed on an incision that has previously been made in the body, for example on the abdominal wall, and, by application of a strong pushing movement, the assembly made up of trocar mandrel and trocar sleeve is driven through the abdominal wall Into the abdominal cavity. After this procedure, the trocar mandrel is withdrawn. In doing this, the trocar sleeve can in theory be pushed into the abdominal cavity until the valve housing comes to lie on the abdominal wall. It is not possible to rule out the possibility of the distally protruding trocar mandrel causing injuries inside the body as the trocar sleeve is being driven in. If a trocar mandrel is used which is considerably longer than the trocar sleeve, there is a considerable risk of injury if the trocar mandrel is driven in too far.

There can be even farther-reaching consequences when using a medical instrument through whose shaft instruments for detaching tissue are guided. An example of such an instrument is a morcellator.

Such a morcellator is described, for example, by the Applicant under the name "Rotocut" in the catalog Endoworld Gyn 20-1-E/11-2004. A morcellator has a relatively large housing of great diameter in which a motor is received, and, extending from the distal end, there is a hollow shaft which, in the same way as described above in the context of a trocar, can be guided into a body. A cutting tool that can be driven by the motor is received in the shaft, said cutting tool likewise comprising a tube and being provided with a cutting edge about its distal periphery. A gripping tool can additionally be pushed through the tubular cutting tool, for example in order to grip and hold a tissue that is to be detached by the cutter. In the actual process of tissue removal, the morcellator is driven forward by a certain distance that corresponds to the height of the tissue that is to be detached, which height will differ according to the anatomical circumstances and the pathological case in question. Here too, the dexterity of the operating surgeon again dictates how far he pushes the morcellator forward into the body during the tissue removal. Pushing it in too far would mean detaching not only the pathological tissue, but also the subjacent healthy tissue, which of course is to be avoided.

It is therefore object of the invention to provide a spacer which should also be able to be applied, if appropriate, when the instrument is already inserted in the body.

SUMMARY OF THE INVENTION

This object is achieved by a spacer for limiting the depth of insertion, which has a distal abutment for bearing on the body and a spacer element extending along a length portion and which moreover has a device for releasably mounting the spacer on the medical instrument and comprises an aperture via which the spacer can be mounted on the shaft, the aperture being designed as a lateral slit aperture via which the spacer can be fitted from the side onto the shaft.

The provision of a spacer now makes it possible in principle to vary the depth of insertion, in particular to limit this depth of insertion. By providing a distal abutment which can come to bear on the body, the depth of insertion of the shaft is limited by the spacer and no longer by other structural parts of the instrument. The spacer comprises a spacer element which extends along a length portion of the shaft and which either itself limits the extent by which the depth of insertion is limited or at least determines this extent via the distal abutment. By providing a device for releasably mounting the spacer on the instrument, the spacer can be fitted on the medical instrument when the need arises. Moreover, the fact that it is releasable means that the spacer can be set to respectively desired spacer positions on the medical instrument, i.e. a position permitting or limiting the different depths of insertion of the shaft. This can be done in steps or also steplessly, so that it can be adapted with the greatest possible variation to the anatomical circumstances in question.

The provision of the aperture has the advantage that the spacer can be mounted or fitted directly on the structural part of the instrument whose depth of insertion is to be limited, namely on the shaft, so that the extent by which the depth of insertion is limited can be particularly easily ascertained and set. For example, if the shaft has a theoretical depth of insertion of 15 cm, but is only to be pushed in by a maximum of 10 cm, the depth of insertion can be reduced by the required 5 cm by means of suitable positioning of the spacer on the shaft.

By designing the aperture as a lateral slit aperture, a spacer can be fitted from the side onto the shaft, specifically at any desired time of the procedure.

This measure has the considerable advantage that the spacer can be fitted onto the shaft even when the medical instrument has already been inserted into the body.

In another embodiment of the invention, several spacers can be coupled to one another.

This measure has the advantage that the extent by which the depth of insertion is limited can be modified by coupling several spacers to one another. If we take the above example with the spacer having the lateral aperture, then, after a spacer has been pushed on from the side and the depth of insertion is to be further limited, an additional spacer can simply be pushed on.

This can either be done by a further spacer being pushed onto the already fitted spacer, or by the latter being briefly removed and coupled to a second spacer and by the assembly of the two or more spacers then being mounted again on the shaft.

In another embodiment, the abutment is designed as a planar body.

This measure has the advantage that the insertion procedure does not adversely affect the body, since the forces can be distributed across the planar body. At the same time, even when the insertion movement of the instrument is carried out with relatively great force, it is possible to avoid the instrument being inserted too far as a result of the body tissue being pressed inward.

In another embodiment of the invention, the abutment is designed as a disk-like body.

This measure has the advantage that this disk geometry exerts the aforementioned force or abutment resistance very gently.

In another embodiment of the invention, the spacer element has a first annular flange which projects from the abutment and which merges via a shoulder into a second annular flange of greater diameter.

This embodiment now opens up the possibility of several such spacer elements simply being coupled to one another or stacked on top of one another. At the same time, by means of the corresponding axial length extension of the second annular flange of greater diameter, it is possible to define very specific reductions of the depth of insertion per spacer element, for example at centimeter intervals or two-centimeter intervals or the like.

In another embodiment of the invention, the external diameter of the first annular flange corresponds approximately to the clear internal diameter of the second annular flange.

This measure has the advantage that several such spacer elements of this design can be pushed onto one another and sit relatively firmly on one another. Several spacer elements pushed onto one another then constitute an approximately cylindrical base body which is made up of the respective second annular flanges of greater diameter, and it is only from the uppermost spacer element of the stack that the first annular flange of slightly smaller diameter protrudes, which then merges into the actual abutment, namely the disk-like or planar body.

In another embodiment of the invention, the clear internal diameter of the second annular flange is chosen such that it can be placed on a corresponding projection on the instrument.

This measure now has the considerable advantage that a spacer element can be mounted securely such that it sits in a defined position on the instrument.

Going back to the example with the lateral slit aperture, the spacer can be pushed on from the side at any position along the length of the shaft and, by axial displacement, can be moved in the proximal direction until the second annular flange of greater diameter sits on the corresponding projection on the instrument. If appropriate, further spacer elements can then be fitted onto a spacer element that has already been fitted in this way, or an assembly of several spacer elements fitted on top of one another can also be fitted in the same way. By choice of a suitable dimension, it is possible for the second annular flange of greater diameter to be pushed or clipped onto the projection by overcoming a certain resistance, such that the spacer element fitted in this way sits securely and immovably, but also releasably, on the instrument. This embodiment, that is to say the interaction of the projection and the second annular flange of greater diameter, constitutes part of the device for mounting the spacer on the instrument.

In another embodiment of the invention, the device for the releasable mounting comprises a locking screw via which a spacer fitted on the shaft of the instrument can be locked on the shaft.

This measure has the advantage that, after a spacer is located in the desired position, it can be locked in this position via the locking screw.

In another embodiment of the invention, the width of the slit aperture in the spacer is slightly smaller than the external diameter of the shaft, so that the spacer can be engaged with a press fit onto the shaft.

This measure has the advantage that the spacer, while still being releasable, can nevertheless be engaged already with a certain press fit.

Depending on the further design of the device, the spacer can now remain in this press fit on the shaft, if this is sufficient and offers enough resistance against displacement, or, if appropriate, it can be additionally secured by a locking screw. If the press fit is chosen such that the spacer can be pushed onto the shaft from the side, but can still be moved axially along the shaft, this embodiment serves merely to ensure that the spacer can initially be fitted in a captive manner on the shaft and, by displacement, can then be brought, still captive, to the aforementioned projection for example.

This reveals the variability of the embodiment of the device for releasable mounting, and, by means of this variability and, for example, a suitable choice of material, it is possible to obtain spacers for multiple applications or also only for disposable use.

It will be appreciated that the aforementioned features and the features still to be explained below can be used not only in the respectively cited combination, but also in other combinations or singly, without departing from the scope of the present invention.

BRIEF DESCRIPTION OF THE DRAWINGS

The invention is described and explained in greater detail below on the basis of two selected illustrative embodiments and with reference to the attached drawings, in which:

FIG. 8 shows a representation comparable to FIGS. 6 and 7 and depicting a morcellator onto which a further illustrative embodiment of a spacer in the form of a slit disk is mounted, and FIG. 9 shows a plan view of the spacer depicted in FIG. 8.

DETAILED DESCRIPTION OF PREFERRED EMBODIMENTS

Figure 1:
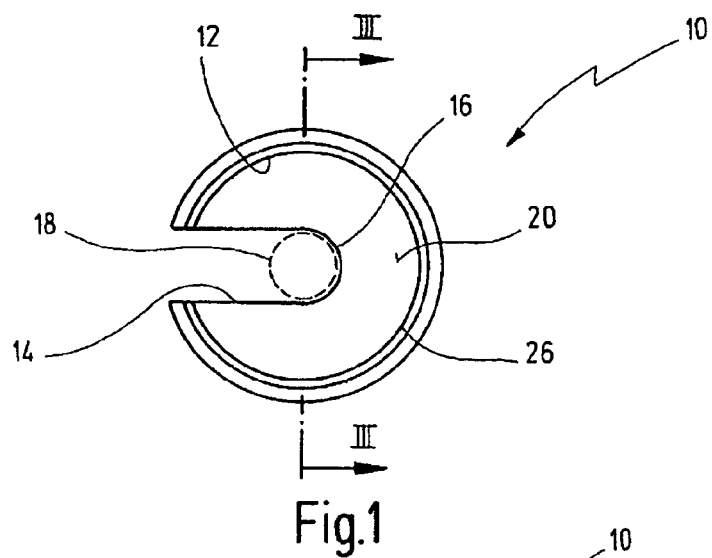
FIG. 1 shows a plan view of the distal abutment of a first illustrative embodiment of a spacer.

An illustrative embodiment of a spacer shown in FIGS. 1 to 4 is designated in its entirety by reference number 10.

The spacer 10, at the distal end, is roughly in the form of a disk 12 in which a laterally opening slit aperture 14 Is formed. The slit aperture 14 has a circular base 16 whose diameter and position are such that the spacer 10 can be pushed from the side onto a shaft 18 of an instrument that will be described below, specifically in such a way that the shaft 18 then comes to lie approximately in the center of the slit disk 12, as is indicated by the dashed line in FIG. 1.

Figure 2:
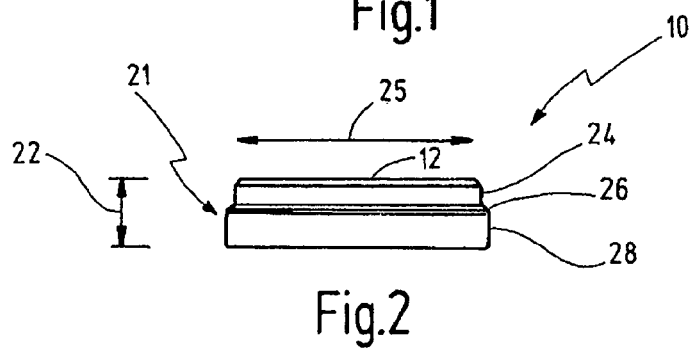
FIG. 2 shows a side view of the spacer from FIG. 1.

It will be seen from the side view in FIG. 2 that a first annular flange 24 extends from the disk 12 and merges via a shoulder 26 into a second annular flange 28 of somewhat greater diameter. These form a spacer element 21 that extends along a length portion 22.

Figure 3:
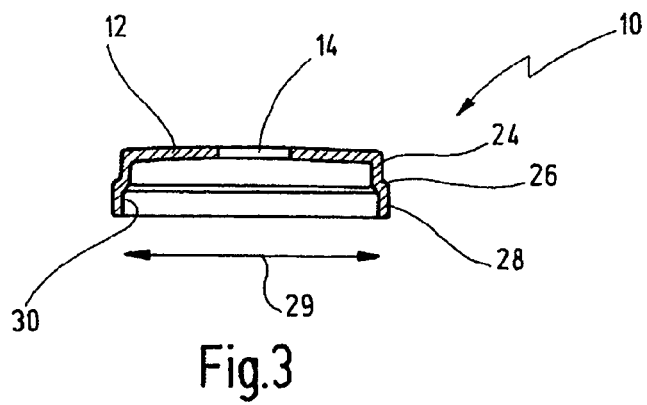
FIG. 3 shows a cross section along the line III-III in FIG. 1.

It will be seen from the views in FIGS. 2 and 3 that the external diameter 25 of the first annular flange 24 corresponds approximately to the clear internal diameter 29 of the second annular flange 28. In this way it is possible to fit or to stack several spacers 10 on top of one another, namely by placing the second annular flange 28 of a spacer 10' onto the first annular flange 24 of a preceding spacer 10.

Figure 4:
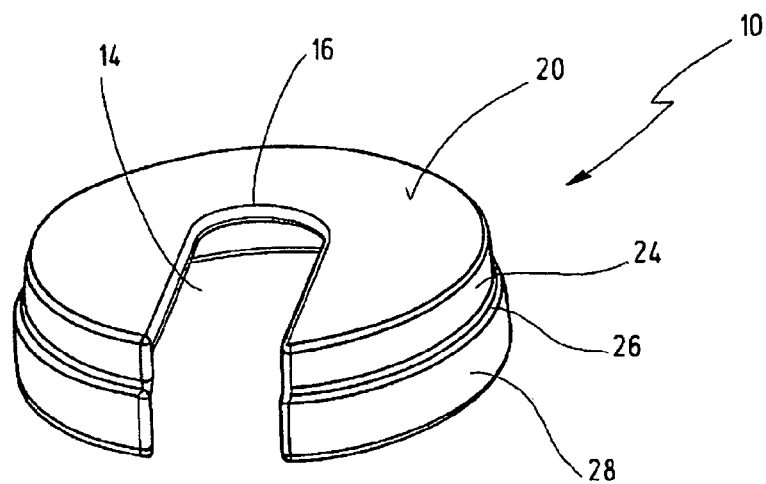
FIG. 4 shows a perspective view of the spacer from FIG. 1.
Figure 5:
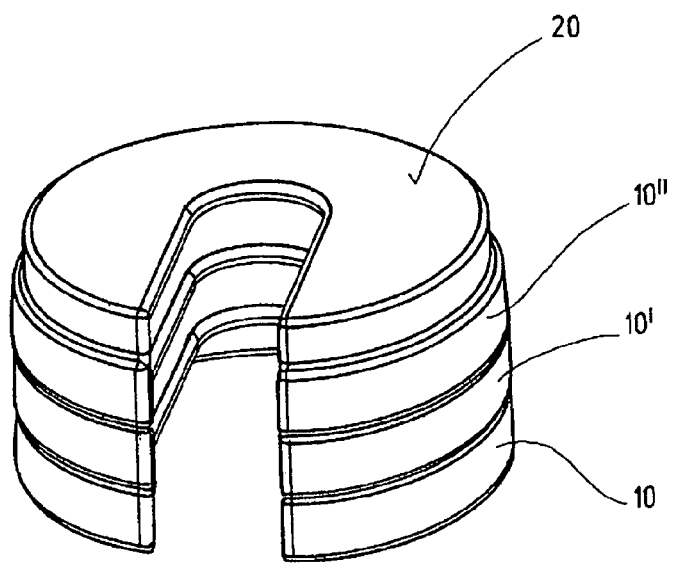
FIG. 5 shows a perspective view of three spacers from FIG. 4 that have been stacked or fitted on top of one another.

FIG. 5 shows a situation in which a second spacer 10' is fitted onto a first spacer 10, as shown in FIG. 4, and a third spacer 10" is in turn fitted onto the second spacer 10'. The respective top face of the uppermost disk-shaped body of a spacer forms a corresponding abutment 20, as will be described in more detail below with reference to FIGS. 6 and 7.

The spacers 10, 10', 10" can be made of plastic, but they can also be made of metal.

Figure 6:
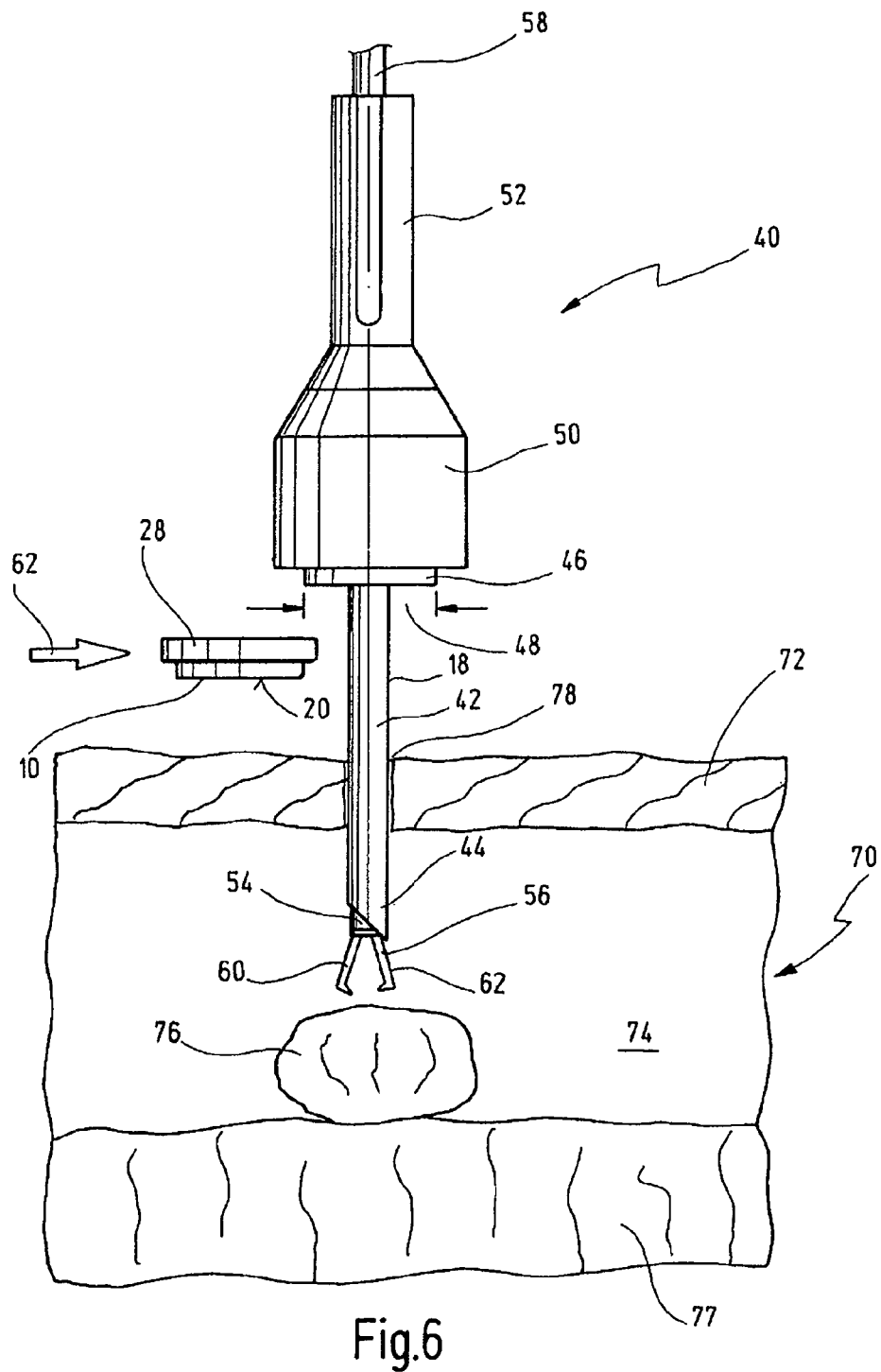
FIG. 6 shows a highly diagrammatic representation, in partial cross section, of a situation in which the spacer shown in FIGS. 1-4 is to be fitted onto a shaft of a medical instrument in the form of a morcellator, the medical instrument having already been introduced into a body.

FIG. 6 shows a situation in which the sleeve 42 of a medical instrument 40 is pushed through an incision 78 in the skin 72 of a human body 70 and into a corresponding internal cavity 74.

The medical instrument 40 is designed as a morcellator.

The medical instrument 40 has a sleeve 42 which is designed as a shaft 18, as has been described above.

The sleeve 42 has a beveled tip 44 at the distal end. The sleeve 42 is received in a housing 50 whose diameter is a multiple of the diameter of the sleeve 42. At the proximal end, the housing 50 opens into a rod-shaped handle 52 via which the morcellator can be gripped by hand.

At the proximal end, the sleeve 42 is provided with an annular projection 46 via which the sleeve 42 can be mounted on the housing 50. The projection 46 is approximately disk-shaped and has an external diameter 48 which, as will be described below, corresponds approximately to the clear internal diameter 29 of the second annular flange 28 of the spacer 10.

A similarly tubular or sleeve-shaped cutting tool 54 whose distal end is provided with a rotary cutter 56 is received in the inside of the sleeve 42. A forceps 58 is pushed through the inside of the sleeve-shaped cutting tool 54, its jaw parts 60 and 62 protruding distally from the cutting tool 54 and spreading in a straight line.

The jaw parts 60 and 62 are used for gripping and holding a portion of tissue 76 that is to be detached, so that, with the jaw parts 60, 62 then closed, this gripped area of tissue can be cut off by the cutting tool 54 and, if appropriate, immediately sectioned through the inner cavity. It will be seen from the representation in FIG. 6 that the sleeve 42 or shaft 18 of the instrument 40 can theoretically be pushed into the body 70 until the distal end of the projection 46 comes to lie on the outside of the skin 72. In this case, however, the cutting tool 54 would already have passed through the tissue area 76 that is actually to be detached, and it would have penetrated into a subjacent area of healthy tissue 77, which is not to be detached.

In order to limit the depth of insertion of the shaft 18 or sleeve 42 of the instrument 40, one or more spacers 10, 10', 10" can now be pushed on. FIG. 6 shows a situation illustrating how the spacer 10 is guided In a straight line from the side toward the sleeve 42, specifically until said sleeve 42 comes to lie in the base 16 of the lateral slit aperture 14, as is shown in FIG. 1. Depending on its design, the spacer 10 could now remain in this position, for example if the spacer 10 has to be pushed on from the side with such a press force that it can virtually no longer move axially. This can be achieved by suitable choice of the materials and of the dimensions.

If the operating surgeon were to push the instrument 40 in with substantial pressure, it would not be possible to rule out the possibility of the spacer 10 being moved along the sleeve 42 in the proximal direction. This could go so far that the second annular flange 28 of greater diameter comes to sit on the projection 46.

It is therefore possible to provide for this to be the case from the outset, that is to say a spacer 10 is applied until it comes to sit on the projection 46.

Figure 7:
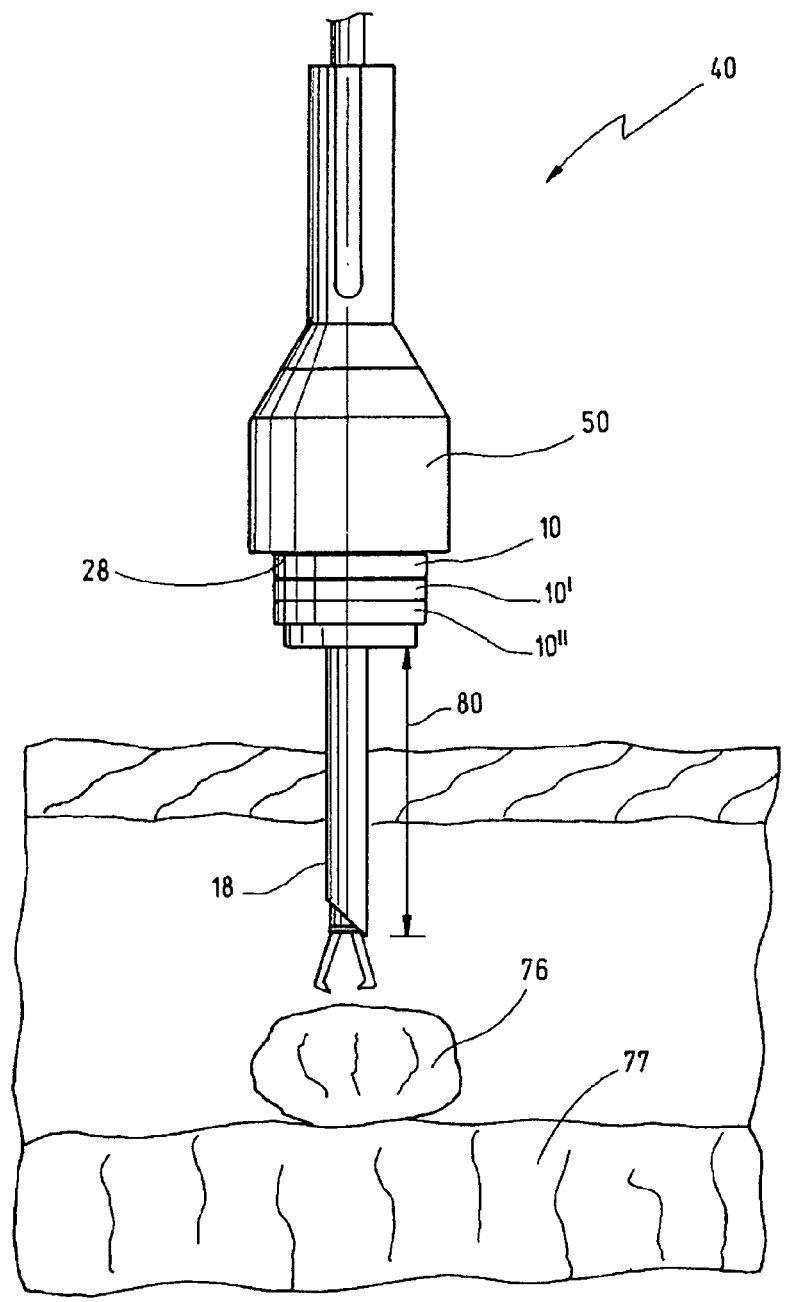
FIG. 7 shows a situation which is comparable to the representation in FIG. 6 and in which the assembly depicted in FIG. 5, made up of three spacers stacked on top of one another, is mounted on the shaft.

If it is desired to limit the depth of insertion by more than the extent of the length portion 22 (see FIG. 2) of the spacer 10, an assembly made up of several spacers can be applied, as is shown in FIG. 7.

Here, an assembly as shown in FIG. 5 has been fitted on the instrument 40, specifically in such a way that the second annular flange 28 of greater diameter of the lowermost spacer element 10 of the stack sits on the projection 46. It will be seen from FIG. 7 that the depth of insertion 80 is correspondingly reduced, namely by an extent that is the sum of the height of the three second annular flanges 28 plus the height of the first annular flange 24 of the uppermost spacer 10" of the stack. This assembly of the three spacers 10, 10', 10" now ensures that the instrument 40 can be pushed in exactly to such an extent that only the tissue 76 that is to be detached can be detached, and not the tissue 77 lying below this.

FIGS. 8 and 9 show a further embodiment of a spacer 90 which has the form of an annular disk 92 provided laterally with a slit aperture 94 whose clear width corresponds approximately to the external diameter of the sleeve 42 of the instrument 40, which is identical in design to the aforementioned instrument 40, that is to say is once again a morcellator.

The body of the annular disk 92 receives a radially extending locking screw 96 which can be screwed into the slit 94 and in this way secures the annular disk 92 in a defined position on the shaft 42.

The longitudinal axis of the locking screw 96 is at approximately 90° to the longitudinal axis of the slit aperture 94.

By loosening the locking screw 96, the spacer 90 can be moved in the axial direction along the sleeve 42, as is indicated by a double arrow 97 in FIG. 8. When the desired position is reached, the spacer 90 is fixed by tightening the locking screw 96 at a defined position. It will be noted that the distal face of the annular disk 92 forms an abutment 93. This abutment 93 then limits the depth of insertion 98 of the sleeve 42 into the interior 74 of the body 70, as has been described above.

The invention claimed is:

1. A stackable spacer extending along a length section of the shaft of a medical instrument for limiting a depth of insertion of the shaft into a body of a patient, the spacer comprising:

an even disk for bearing on a body of a patient, the even disk having a lateral slit, and a first annular flange which projects from said disk, and which merges via a shoulder into a second annular flange of greater diameter, the first flange and the second flange extending approximately perpendicular to said disk, the external diameter of the first annular flange matching a clear internal diameter of the second annular flange, wherein the clear inner diameter of the second flange is placed onto a corresponding projection projection distally on said medical instrument, and wherein the spacer is mounted from a side on to said shaft via the lateral, slit in said even disk.

2. The spacer of claim 1, wherein several spacers are coupled to one another.

3. The spacer of claim 1, wherein said even disk is designed as a planar body.

4. The spacer of claim 1, wherein the external diameter of the first annular flange corresponds to the clear inner diameter of the second annular flange.

5. The spacer of claim 1, wherein the disk has a circular base whose diameter and position are such that said shaft lies approximately in the center of said even disk when the spacer is mounted on said shaft.

6. The spacer of claim 1, wherein the second annular flange of the spacer fits onto a first annular flange of a second spacer when the first spacer is stacked on the second spacer, resulting in a firm sit of the first spacer stacked on the second spacer, wherein the second spacer includes an even disk for bearing on a body of a patient, the even disk having a lateral slit.

7. The spacer of claim 6, wherein the lateral slit of the first spacer is coplanar with the lateral slit of the second spacer allowing for the first spacer and the second spacer to be mounted from a side on to said shaft.

8. The spacer of claim 6, wherein the second spacer includes a second annular flange, and wherein the second annular flange of the second spacer fits onto a first annular flange of a third spacer when the second spacer is stacked on the third spacer, resulting in a firm sit of the second spacer stacked on the third spacer.

9. The spacer of claim 1, wherein the spacer is stackable upon at least one other spacer to form a stack of spacers fitting upon one other.

10. A medical instrument comprising:

a shaft;

at least one stackable spacer extending along a length section of said shaft for limiting a depth of insertion of said shaft into a body of a patient, said at least one spacer comprising:

a distal abutment in form of an even disk for bearing on a body of a patient, and first annular flange which projects from said disk, and which merges via a shoulder into a second annular flange of greater diameter, the external diameter of the first annual flange matching a clear internal diameter of the second annular flange, the first and second flange extending approximately perpendicular to said disk, the second annular flange of one spacer fitting onto the first annular flange of a second spacer when the one spacer is stacked on the second spacer, resulting in a firm sit of said one spacer stacked on the second spacer;

a device for releasably mounting said at least one spacer on said medical instrument, said device having an aperture via which said spacer can be mounted on said shaft, said aperture being designed as a lateral slit in said disk aperture via which said spacer can be fitted from a side on to said shaft, and a projection projecting distally on said medical instrument, the clear inner diameter of the second annular flange of said spacer able to be placed onto said projection.

11. The medical instrument of claim 10, wherein a width of said slit aperture is slightly smaller than an external diameter of said shaft of said instrument, so that said spacer can be engaged with a press fit onto said shaft.

12. The medical instrument of claim 10, wherein several spacers are mounted on said shaft.

13. The medical instrument of claim 10, wherein said projection has an external diameter that corresponds to the clear internal diameter of the second annular flange of the at least one spacer.

14. The medical instrument of claim 10, wherein the at least one spacer is stackable upon at least one other spacer to form a stack of spacers fitting upon one other.

15. A spacer extending along a length section of the shaft of a medical instrument for limiting a depth of insertion of the shaft into a body of a patient, the spacer comprising:

an even disk for bearing on a body of a patient, the even disk having a body with a slit aperture whose width corresponds to the external diameter of the shaft, and a locking screw that is screwed into the slit aperture to secure the disk on the shaft in a defined position of the shaft.

16. The spacer of claim 15, wherein the locking screw is at approximately 90° to the longitudinal axis of the slit aperture.

17. The spacer of claim 15, wherein if the locking screw is loosened, the spacer can be moved in the axial direction along the shaft.

18. The spacer of claim 15, wherein the distal face of the disk forms the abutment to limit the depth of insertion of the shaft into the body of the patient.

* * * * *